(12) United States Patent
Georgeson et al.

(10) Patent No.: US 9,518,879 B2
(45) Date of Patent: Dec. 13, 2016

(54) BLUNT IMPACT INDICATOR METHODS

(71) Applicant: The Boeing Company, Chicago, IL (US)

(72) Inventors: Gary E. Georgeson, Tacoma, WA (US); William Joseph Tapia, Kapowsin, WA (US)

(73) Assignee: The Boeing Company, Chicago, IL (US)

( * ) Notice: Subject to any disclaimer, the term of this patent is extended or adjusted under 35 U.S.C. 154(b) by 318 days.

(21) Appl. No.: 14/337,285

(22) Filed: Jul. 22, 2014

(65) Prior Publication Data

US 2016/0178463 A1 Jun. 23, 2016

(51) Int. Cl.
*G01L 1/24* (2006.01)
*G01L 5/00* (2006.01)
(Continued)

(52) U.S. Cl.
CPC .............. *G01L 1/247* (2013.01); *B64F 5/0045* (2013.01); *G01L 5/0052* (2013.01); *G01L 5/14* (2013.01);
(Continued)

(58) Field of Classification Search
CPC .......... G01L 1/247; G01L 5/00; G01L 5/0052; G01L 5/14; G01M 5/00; G01M 5/0083; G01N 3/00; G01N 25/72; G01N 27/20; G01N 27/90; G01P 15/006; G01P 15/008; G01P 15/038; G01P 15/04; G01P 15/06; H01H 29/00; H01H 29/002; H01H 29/004; H01H 35/14
(Continued)

(56) References Cited

U.S. PATENT DOCUMENTS 2,643,285 A * 6/1953 Cranford .............. G01R 31/022
324/513
3,469,439 A * 9/1969 Roberts et al. .......... B01J 13/02
428/402.2
(Continued)

FOREIGN PATENT DOCUMENTS

DE 102013200693 A1 7/2014
FR 2356540 A1 * 1/1978 ............. B60R 19/18
GB 2194062 A 2/1988

OTHER PUBLICATIONS

Extended European Search Report for European Application No. 15174164.2 (European counterpart of the instant patent application) dated Apr. 13, 2016.
(Continued)

*Primary Examiner* — Richard A Smith
(74) *Attorney, Agent, or Firm* — Ostrager Chong Flaherty & Broitman P.C.

(57) ABSTRACT

Systems and methods using fluid-filled hollow microspheres to assist in monitoring or indicating high-energy blunt impacts on structures such as aircraft. A multiplicity of microspheres may be adhered to or embedded in a coating applied on a surface of a substrate (e.g., a tape or an appliqué), which substrate in turn can be adhered to a surface of a structure to be monitored. The microspheres are designed to rupture at one or more specified pressure thresholds. In some embodiments, the microspheres are filled with electrically conductive fluid which, if released from ruptured microsphere, changes the electromagnetic state of the substrate. In response to the detection of a sufficiently large change in the electromagnetic state of the substrate, a blunt impact indication is generated. The impact site may then undergo non-destructive inspection.

17 Claims, 10 Drawing Sheets

(51) Int. Cl.
*G01M 5/00* (2006.01)
*G01N 3/00* (2006.01)
*G01N 27/90* (2006.01)
*B64F 5/00* (2006.01)
*G01P 15/06* (2006.01)
*G01L 5/14* (2006.01)
*H01H 29/00* (2006.01)
*H01H 35/14* (2006.01)

(52) U.S. Cl.
CPC .............. *G01M 5/0083* (2013.01); *G01N 3/00* (2013.01); *G01N 27/90* (2013.01); *G01P 15/06* (2013.01); *H01H 29/002* (2013.01); *H01H 35/146* (2013.01)

(58) Field of Classification Search
USPC .................. 116/203, 212; 250/462.1; 374/45
See application file for complete search history.

(56) References Cited

U.S. PATENT DOCUMENTS

| | | | |
|---|---|---|---|
| 3,803,485 A | | 4/1974 | Crites et al. |
| 4,799,019 A | * | 1/1989 | Cooley et al. ........ G01R 31/026 324/133 |
| 5,242,830 A | * | 9/1993 | Argy et al. ............. G01P 15/03 116/200 |
| 6,651,488 B2 | * | 11/2003 | Larson, III et al. .. C23C 14/546 427/10 |
| 7,287,902 B2 | | 10/2007 | Safai et al. |
| 7,312,608 B2 | | 12/2007 | Georgeson et al. |
| 7,434,480 B2 | | 10/2008 | Georgeson et al. |
| 7,568,832 B2 | | 8/2009 | Safai et al. |
| 7,647,809 B1 | | 1/2010 | Cooney |
| 7,898,246 B2 | | 3/2011 | Georgeson et al. |
| 8,059,008 B2 | * | 11/2011 | Marincak ............... G01N 27/24 324/691 |
| 8,220,991 B2 | | 7/2012 | Safai et al. |
| 8,691,383 B2 | | 4/2014 | Georgeson et al. |
| 2007/0197383 A1 | * | 8/2007 | Koene et al. .......... B41M 5/124 503/201 |
| 2008/0224879 A1 | | 9/2008 | Zadesky et al. |
| 2008/0277596 A1 | * | 11/2008 | Oxley .................... C09K 11/06 250/462.1 |
| 2011/0262273 A1 | * | 10/2011 | Behnisch et al. ........ F01D 17/02 416/61 |
| 2012/0225294 A1 | | 9/2012 | Georgeson et al. |
| 2012/0279311 A1 | * | 11/2012 | Helmer et al. ..... A63B 24/0021 73/768 |

OTHER PUBLICATIONS

Partial European Search Report, European Application No. 151741642 (European counterpart to the instant application), dated Dec. 9, 2015.

* cited by examiner

BLUNT IMPACT INDICATOR METHODS

BACKGROUND

This disclosure generally relates to systems and methods for monitoring or indicating high-energy impacts on a structure. More particularly, this disclosure relates to systems and methods for measuring the magnitude and location of a high-energy impact event.

When damage to a structural component is suspected, it is customary to evaluate the structural integrity of the possibly damaged component using non-destructive evaluation (NDE) techniques. When NDE techniques are used, it may be difficult to determine specific points of damage quickly because large areas of the structure may need to be scanned. Therefore, it is desirable to have a technique whereby the precise location of damage can be easily determined.

In the aviation industry, an aircraft may be vulnerable to high-energy blunt impacts from support vehicles and ground support equipment such as cargo belt loaders, luggage carts, aircraft refuelers, catering vehicles, ground power units, airport buses and passenger boarding stairs. In response to any indication that a high-energy blunt impact has occurred, the customary first maintenance procedure is to perform a non-destructive evaluation of the impacted area sufficient to determine an appropriate disposition, e.g., repair the damage to the aircraft.

Although methods are known for producing a visual indication of an on-aircraft high-energy blunt impact to a casual observer by the placement of impact tape (comprising rupturable microspheres filled with colored indicator fluid) on the surface of an aircraft structure which is vulnerable to such impacts, in some instances visual indication of surface damage may not be wanted.

There is scope for improvements in existing technology for monitoring or indicating high-energy blunt impacts on structures such as aircraft.

SUMMARY

The subject matter disclosed herein is directed to systems and methods using fluid-filled hollow microspheres to assist in monitoring or indicating high-energy blunt impacts on structures such as aircraft. A multiplicity of microspheres may be adhered to or embedded in a coating applied on a surface of a substrate (e.g., a tape or an appliqué), which substrate in turn can be adhered to a surface of a structure to be monitored. The microspheres are designed to rupture at one or more specified pressure thresholds. In some embodiments, the microspheres are filled with electrically conductive fluid which, if released from ruptured microsphere, changes the electromagnetic state of the substrate. In response to the detection of a sufficiently large change in the electromagnetic state of the substrate, a blunt impact indication is generated. The impact site may then undergo non-destructive inspection.

One aspect of the subject matter disclosed in detail below is a blunt impact indicator device comprising: a substrate comprising first and second surfaces; and a multiplicity of rupturable shells disposed in proximity to said first surface of said substrate, the shells having an electrically conductive fluid disposed in an internal volume of the shells. The shells can be hollow microspheres made of dielectric material. The substrate may be in the form of a tape or an appliqué.

In accordance with one implementation, the blunt impact indicator device further comprises: first and second electrical conductors; and a voltage supply connected to the first and second electrical conductors, wherein the first and second electrical conductors are disposed on one side of the first surface of the substrate and spaced apart so that the first and second electrical conductors will be electrically coupled to each other by electrically conductive fluid escaped from the multiplicity of shells and will not be electrically coupled to each other in the absence of electrically conductive fluid from the multiplicity of shells. A meter may be provided for measuring a magnitude of electrical current flowing through the first electrical conductor.

In accordance with another implementation, the blunt impact indicator device further comprises: first and second electrical conductors which are not electrically coupled to each other in the absence of electrically conductive fluid; and a radio-frequency identification circuit connected to the first and second electrical conductors, wherein the first and second electrical conductors are disposed on one side of the first surface of the substrate and configured and spaced so that the first and second electrical conductors can be electrically coupled to each other in the presence of electrically conductive fluid released from the multiplicity of shells. In this implementation, the radio-frequency identification circuit may comprise a transceiver coupled to the first and second electrical conductors and non-volatile memory storing information which uniquely identifies the radio-frequency identification circuit.

In accordance with a further implementation, the blunt impact indicator device further comprises: a first layer of electrically conductive material disposed on the first surface of the substrate; a second layer of electrically conductive material overlying the first layer electrically conductive material with a space therebetween, the multiplicity of shells being disposed in the space; and a voltage supply connected to the first and second layers of electrically conductive material, wherein the first and second layers of electrically conductive material are spaced apart so that the first and second layers of electrically conductive material will be electrically coupled to each other when wetted by electrically conductive fluid released from the multiplicity of shells and will not be electrically coupled to each other in the absence of electrically conductive fluid from the multiplicity of shells.

Another aspect of the subject matter disclosed in detail below is a blunt impact indicator device comprising: a substrate; a breakable electrical conductor disposed on or embedded in the substrate and having first and second terminals; a voltage supply connected to the first and second terminals of the breakable electrical conductor; and a continuity indicator electrically connected to the breakable electrical conductor. Optionally, the blunt impact indicator device further comprises: a multiplicity of rupturable shells disposed in proximity to a surface of the substrate, the shells being distributed over an area encompassing the breakable electrical conductor, each shell having an internal volume; and an electrically conductive fluid disposed in the internal volumes of respective shells of the multiplicity of shells.

A further aspect of the subject matter disclosed herein is a method for monitoring a structure for damage due to blunt impact, comprising: attaching a substrate to a surface of the structure, the substrate comprising a multiplicity of rupturable shells adhered thereto or embedded therein, each shell having an internal volume, and an electrically conductive fluid disposed in the internal volumes of respective shells of the multiplicity of shells; and detecting a change in electrical conductivity of the substrate. In accordance with one embodiment, the step of detecting a change in electrical conductivity of the substrate comprises: placing a coil in proximity to the substrate; causing alternating current to flow through the coil during first and second time intervals, a magnitude of the alternating current and a distance separating the coil from the substrate being selected for inducing eddy currents in the substrate; and measuring any difference between a first impedance of the coil during the first time interval and a second impedance of the coil during the second time interval. Optionally, the step of detecting a change in electrical conductivity of the substrate further comprises: determining whether a difference between the first and second impedances is greater than a specified threshold; and performing non-destructive inspection in the area of the structure which the coil is in proximity to if the difference between the first and second impedances is greater than the specified threshold.

Yet another aspect is a method for monitoring a structure for damage due to blunt impact, comprising: attaching a substrate to a surface of a structure, the substrate comprising a multiplicity of rupturable shells disposed in proximity to a surface of the substrate, each shell having an internal volume, and an electrically conductive fluid disposed in the internal volumes of respective shells of the multiplicity of shells; and detecting a change in thermal state of the substrate which is indicative of escape of electrically conductive fluid from the shells. In accordance with one embodiment, the step of detecting a change in thermal state of the substrate comprises performing the following steps during first and second intervals of time which do not overlap: (a) placing a coil in proximity to the substrate; (b) causing alternating current to flow through the coil while the coil is in proximity to the substrate; (c) after the substrate has been heated in an area during step (b) due to eddy currents induced in the electrically conductive fluid by the alternating current in the coil, removing the coil; and (d) after the coil has been removed, acquiring a thermal image of the area of the heated substrate using a thermal imaging camera. Preferably, the step of detecting a change in thermal state of the substrate further comprises: comparing a first thermal image acquired during the first interval of time with a second thermal image acquired during the second interval of time. The method may further comprise displaying an image representing differences between the first and second thermal images.

Another aspect is a method for monitoring a structure for damage due to blunt impact, comprising: placing a radio-frequency identification circuit and first and second serpentine electrical conductors on a substrate, the first and second serpentine electrical conductors having respective first terminals electrically connected to respective terminals of the radio-frequency identification circuit and respective second terminals which are not electrically connected to each other; placing a multiplicity of rupturable shells over the first and second serpentine electrical conductors, each shell having an internal volume at least partially filled with electrically conductive fluid; and interrogating the radio-frequency identification circuit by transmitting a radio-frequency signal through a volume of space intersected by radio-frequency identification circuit, wherein any response to the interrogation by the radio-frequency identification circuit will have a frequency which is a function of an impedance of an antenna formed if the first and second serpentine electrical conductors are electrically coupled to each other by electrically conductive fluid escaped from the multiplicity of shells.

A further aspect of the disclosed subject matter is a blunt impact indicator device, comprising: a substrate having a surface; a first multiplicity of rupturable shells disposed in proximity to the surface of the substrate, each shell of the first multiplicity having an internal volume; a first fluid having a first pH level disposed in the internal volumes of respective shells of the first multiplicity of shells; and a layer of pH-sensitive material disposed adjacent to the first multiplicity of rupturable shells. This blunt impact indicator device may further comprise: a second multiplicity of rupturable shells intermingled with the first multiplicity of rupturable shells, each shell of the second multiplicity having an internal volume; and a second fluid having a second pH level, different than the first pH level, disposed in the internal volumes of respective shells of the second multiplicity of shells.

Other aspects of systems and methods for monitoring or indicating high-energy blunt impacts on structures such as aircraft are disclosed and claimed below.

BRIEF DESCRIPTION OF THE DRAWINGS

FIG. 7A shows the system when all microspheres are intact, while FIG. 7B shows the system after some microspheres have been ruptured and electrically conductive fluid has been released.

Reference will hereinafter be made to the drawings in which similar elements in different drawings bear the same reference numerals.

DETAILED DESCRIPTION

Various embodiments of blunt impact indicators that employ fluid-filled microspheres will now be described in detail for purposes of illustration only. These blunt impact indicators may be applied on a surface of a structure in the form of a substrate (e.g., a tape or an appliqué) with an adhesive backing. The microspheres may be adhered to the substrate or embedded in a coating applied on the substrate.

Figure 1:
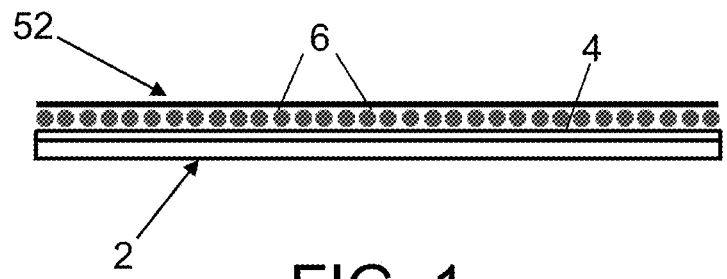
FIG. 1 is a diagram representing a side view of a blunt impact indicator tape comprising rupturable microspheres filled with electrically conductive fluid in accordance with some embodiments.

A first illustrative embodiment of a blunt impact indicator of the foregoing type is schematically depicted in FIG. 1. This blunt impact indicator comprises a substrate 2 having a multiplicity of hollow microspheres 6 attached to and distributed on one surface of substrate 2 by means of a layer 4 of adhesive material (hereinafter "adhesive layer 4"). Optionally the microspheres 6 are covered by a cover layer 52.

The substrate 2 may take different forms. In some cases, the substrate 2 may take the form of a tape comprising a thin strip of plastic material. In other cases, the substrate may take the form of an appliqué comprising a thin sheet of plastic material. The terms "tape" and "appliqué", as used herein, respectively refer to substrates having different ranges of width, with the width of a tape being less than the width of an appliqué. Tape or appliqué can be cut to fit and affixed to the surface of a structure, for example, an aircraft.

Figure 2:
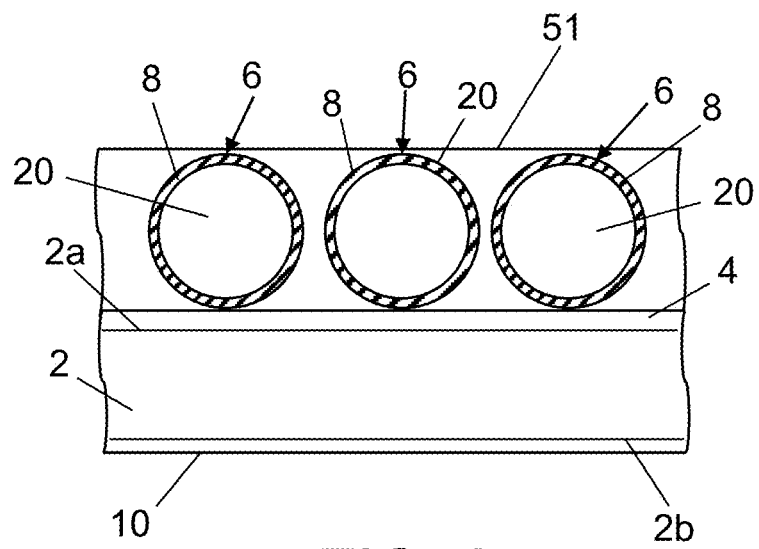
FIG. 2 is a diagram representing a sectional view of a portion of a blunt impact indicator tape in accordance with an alternative embodiment.

Alternatively, as shown in the sectional view of FIG. 2, the microspheres 6 can be embedded in a coating 51 applied on the exterior surface of a substrate 2. The adhesive layer 4 is adhered to a first surface 2a of substrate 2, while an adhesive backing 10 is adhered to a second surface 2b of substrate 2. Optionally, the substrate 2 may further comprise a release film (not shown) which covers and protects the adhesive backing 10 prior to the substrate 2 being adhered to a surface of a structure (not shown in FIGS. 1 and 2).

As seen in FIG. 2, each microsphere 6 comprises a shell 8 that bounds an interior volume when the shell 8 is intact. Each shell 8 can be made of dielectric material having a specified burst strength. In some applications, the shells 8 may have approximately the same burst strength; in other applications different subgroups of shells 8 may have different burst strengths.

Still referring to FIG. 2, the interior volume of each shell 8 is filled (or partially filled) with electrically conductive fluid 20. When an underlying structure (not shown in FIGS. 1 and 2), to which the blunt impact indicator is attached, is subjected to a blunt impact of sufficient magnitude to cause at least some of the multiplicity of shells 8 to rupture, some or all of the electrically conductive fluid 20 will bleed, leak or otherwise escape from the ruptured shells to form a puddle or other collection of fluid in the area of the blunt impact for purposes which will be hereinafter described.

As depicted in FIG. 2, the blunt impact indicator device preferably comprises a multiplicity of closely packed hollow microspheres 6. The dielectric shells 8 of microspheres 6 may be made of glass, plastic or ceramic. However, it is not essential to practice of the invention that the shells 8 be spherical. Other hollow structures (i.e., not spherical) can be employed. The electrically conductive fluid 20 may be any suitable fluid base, including but not limited to a colloidal graphite suspension (e.g., a preparation of fine, pure colloidal graphite in water), which can be diluted with other additives (surfactants, solvents, anti-freeze, etc.) to meet the requirements of a particular environmental envelope.

The release of electrically conductive fluid 20 can change the electromagnetic behavior of the structure in the area of blunt impact. More specifically, the electromagnetic behavior of the structure after electrically conductive fluid has escaped from ruptured microspheres in an impact area will differ from the electromagnetic behavior of the same area when the microspheres are intact (in which case the individual volumes of electrically conductive fluid inside the hollow microspheres are insulated from each other by the intact dielectric shells). This change in electromagnetic properties due to blunt impact can be detected in different ways.

Figure 3:
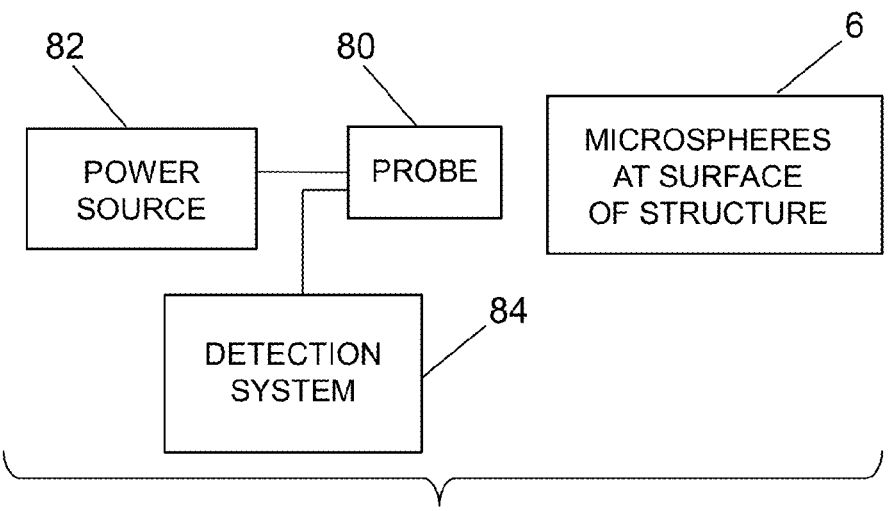
FIG. 3 is a block diagram showing components of an apparatus for nondestructive inspection of a structure using a probe comprising an induction coil for detecting magnetic field disturbances caused by the escape of electrically conductive fluid from hollow microspheres distributed on a surface or in a surface layer of the structure.

FIG. 3 is a block diagram showing components of an apparatus for nondestructive inspection of a structure using a probe 80 comprising an induction coil (not shown in FIG. 3) connected to a power source 82 and to a detection system 84 which detects magnetic field disturbances caused by the escape of electrically conductive fluid from hollow microspheres 6 distributed on a surface or in a surface layer of the inspected structure. The inspected structure may be a skin on a portion of an aircraft, such as a fuselage.

In accordance with one embodiment, the probe 80 is placed in proximity to the area being inspected. Then the power source 82 is turned on. The power source 82 generates an alternating current at a specified frequency, which alternating current flows through the induction coil of probe 80. The resulting waves of electromagnetic radiation emanating from the coil in turn induce eddy currents in any electrically conductors in proximity (e.g., any electrically conductive fluid escaped from ruptured microspheres on a surface or in a surface layer of the structure being inspected). These eddy currents in turn generate more waves of electromagnetic radiation, thereby disturbing the magnetic field being produced by the driven induction coil.

Still referring to FIG. 3, the detection system 84 may comprise circuitry (e.g., a processor) configured to quantify the disturbance or change in the magnetic field produced by the induction coil. In one example, the disturbance or change in magnetic field is detected through a change in the inductive reactance of probe 80. The detection system 84 may further include a display to present the changes in inductive reactance from disturbances to the magnetic field such that a technician can visualize those changes as he/she moves the probe 80 over different sections of the structure being inspected.

In the example depicted in FIG. 3, probe 80 may be a hand-held unit that is moveable by the technician performing the inspection. Detection system 84 may be a hard-wired electronic circuit configured or a processor programmed to convert changes in the probe's inductive reactance, after microspheres 6 have been ruptured, into electrical signals representing parametric data which can then be compared to reference parametric data, stored in memory, which was previously acquired when the microspheres 6 were intact, i.e., pre-blunt impact event.

Figure 4:
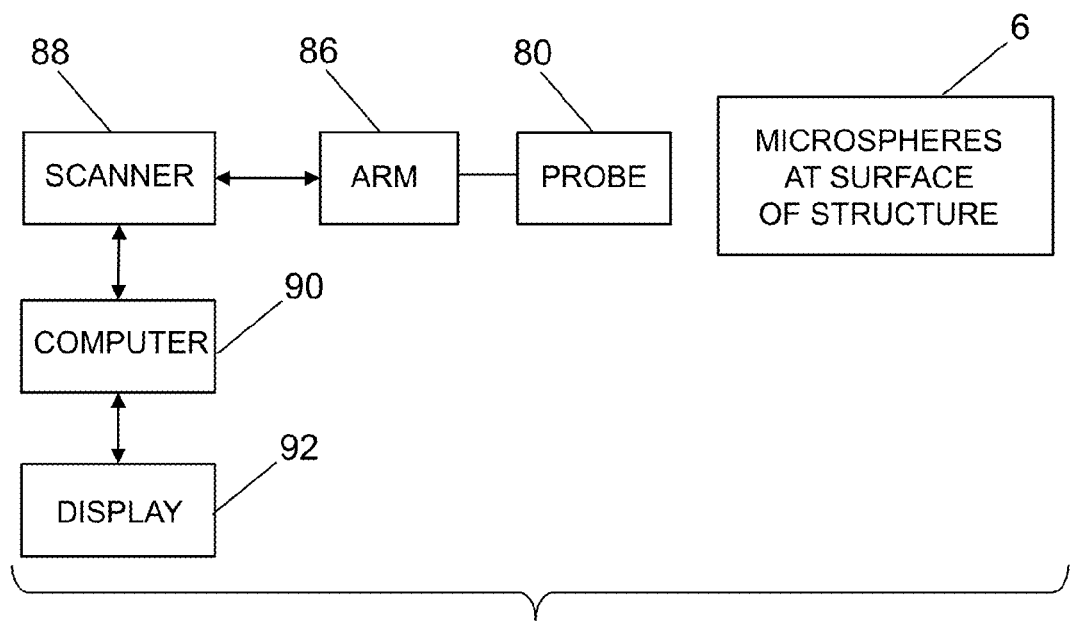
FIG. 4 is a block diagram showing components of an automated scanning apparatus for nondestructive inspection of a structure using a probe comprising an induction coil for detecting magnetic field disturbances caused by the escape of electrically conductive fluid from hollow microspheres distributed on a surface or in a surface layer of the structure.

FIG. 4 shows components of an automated scanning apparatus for nondestructive inspection of a structure using a probe comprising an induction coil. Again the induction coil can be used to detect magnetic field disturbances attributable to the presence of electrically conductive fluid leaked from hollow microspheres 6 previously distributed on a surface or in a surface layer of the structure. In this embodiment, the probe 80 is mounted to the end effector of an arm 86 of a scanner 88. The system further comprises a computer 90, which controls the scanner 88 and receives inductive reactance data from probe 80 for presentation on a display screen 92. Scanner 88 may also provide a power source for probe 80.

In the example depicted in FIG. 4, the computer 90 generates instructions to direct movement of arm 86 by scanner 88 over and in proximity to the area to be inspected. The power source sends an alternating electric current through the induction coil of probe 80 at a specified frequency to generate a varying magnetic field that intensifies and diminishes as the direction of the current alternates. Again the magnetic field generated by probe 80 causes eddy currents within any electrically conductive fluid escaped from the microspheres 6 due to a blunt impact event, which eddy currents in turn cause disturbances or changes in the magnetic field being generated by probe 80 as it moves in proximity to the area being inspected. The results of scanning different sections of the structure may be presented on display screen 92. This display may be presented as a color-coded display, in which different magnetic field strengths are displayed in different colors.

The probe 80 may be designed or configured to generate magnetic fields having a selected size and strength. In some examples, the size and strength of the magnetic field generated by probe 80 may be configured or selected based on a number of different parameters, such as the frequency of the alternating current, the dimensions and geometry of the probe coil, and the diameter of the coil wire. These parameters and other parameters also may be used to select or generate a magnetic field having a specified shape.

Figure 5:
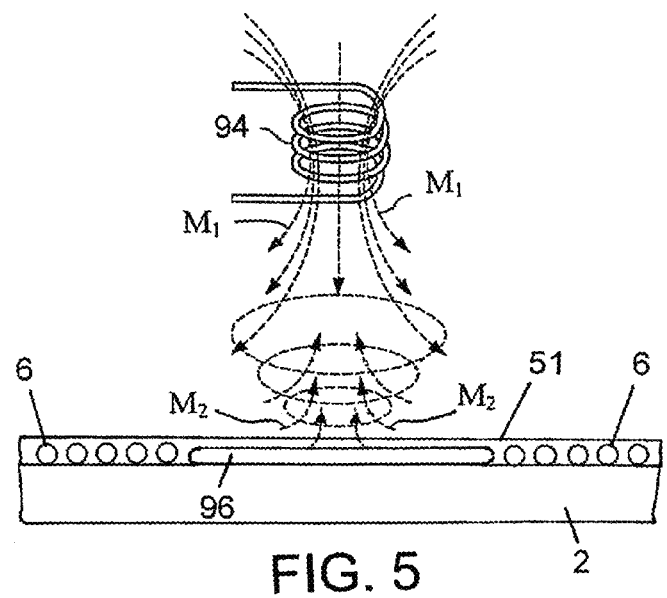
FIG. 5 is a diagram illustrating the use of an induction coil to detect magnetic field disturbances caused by the escape of electrically conductive fluid from hollow microspheres distributed in a surface layer of a structure.

FIG. 5 is a diagram illustrating the use of an induction coil 94 to generate a magnetic field $M_1$ and then detect a magnetic field disturbance $M_2$ due to the presence of a puddle or other collection of electrically conductive fluid 96 which has escaped from ruptured microspheres (not shown) in an inspected area. (Only intact microspheres 6 are shown in FIG. 5 to avoid cluttering the depiction of a collection of electrically conductive fluid 96 with ruptured shells.) In response to coil 94 being driven with an alternating current, the coil 94 generates a varying magnetic field $M_1$, which is indicated for one instant of time by a half-dozen downward-pointing dashed curved arrows in FIG. 5. The eddy currents induced in the electrically conductive fluid 96 in turn generate a varying magnetic field disturbance $M_2$, which is indicated for the same instant of time by a half-dozen upward-pointing dashed curved arrows in FIG. 5. The magnetic field disturbance $M_2$ will vary as the coil is moved over the area being inspected. The magnetic field disturbances $M_2$ may be detected using a measurement circuit connected to the probe. The disturbances are detected in changes in the inductive reactance of the coil 94. Reactance is a form of opposition that electronic components exhibit to the passage of alternating current because of capacitance or inductance. When alternating current passes through a component that has a reactance, energy is alternately stored in and released from a magnetic field or an electric field. In the case of a magnetic field, the reactance is inductive.

The inductance coil 94 depicted in FIG. 5 can be used in any system of the types described above with reference to FIGS. 3 and 4. Electrically conductive fluid 96, when dispersed at blunt impact, can be detected using the inductance coil 94. The dielectric shells of microspheres 6 may be designed with a burst strength which is a function of a specified pressure threshold. In that case, the blunt impact indicator device is capable of detecting any blunt impact that produces a pressure in excess of that threshold. Using an inductance coil to detect blunt impact events has the benefit that no indication of the blunt impact event is visible to a casual observer. Instead an electrical indication can be transmitted to a remote device accessible only to maintenance personnel and, in cases where the structure being inspected is an aircraft, optionally to the flight crew.

In accordance with an alternative implementation, the coil 94 may be part of a hand-held conductive inspection apparatus of the type depicted and described in U.S. Pat. No. 7,312,608.

Figure 6:
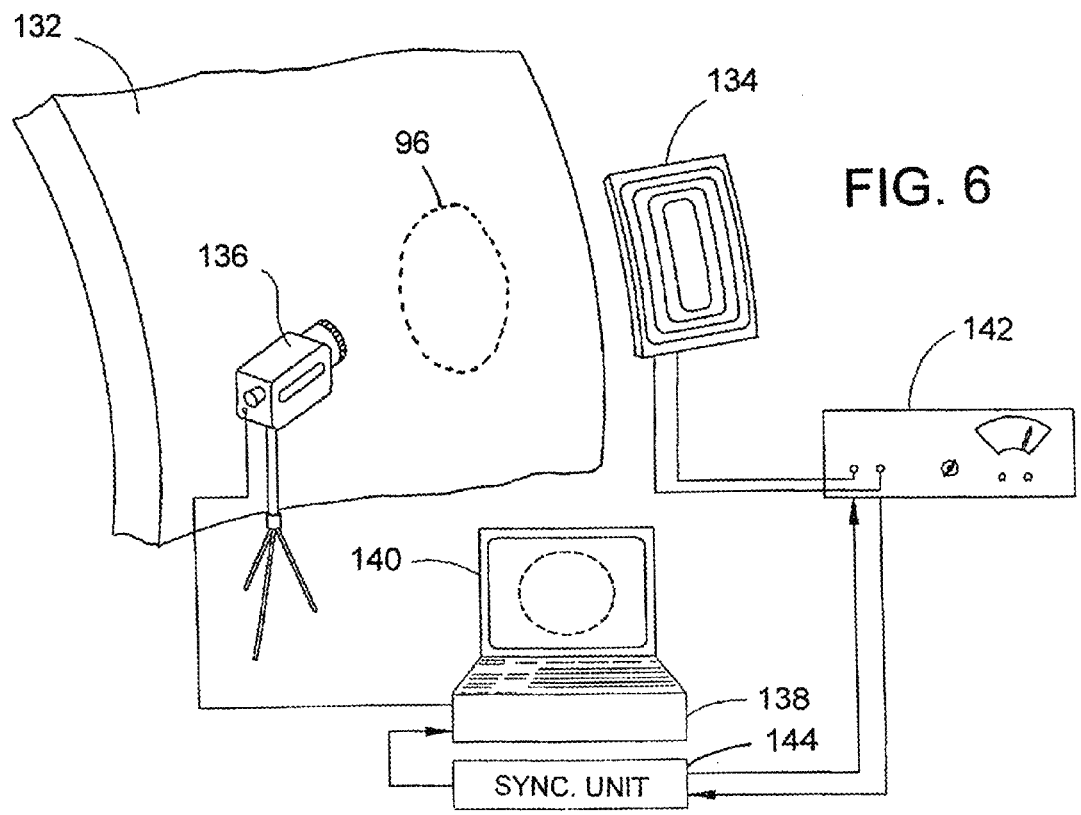
FIG. 6 is a diagram showing components of a system for generating eddy currents in a structure containing electrically conductive fluid-filled microspheres and capturing thermal images before and after a blunt impact event in accordance with an alternative embodiment.

FIG. 6 is a diagram showing components of a system in accordance with an alternative embodiment. The measurement method implemented by this system comprises the following steps performed before and after a blunt impact event: generating eddy currents in an area of a structure containing electrically conductive fluid-filled microspheres; removing the eddy current generator, and then capturing thermal images of the area which has been heated by the eddy currents. For the purpose of illustration, FIG. 6 depicts examination of a portion of a composite aircraft fuselage 132 having an appliqué 96 (indicated by a dashed ellipse) with hollow microspheres adhered to or embedded in a coating on a surface thereof. The electrically conductive media in the hollow microspheres, when dispersed at impact, can be imaged using a high-power radio-frequency (RF) coil 134 to create eddy currents strong enough to raise the temperature locally, with the resulting temperature rise being imaged using a thermal imaging camera 136 (e.g., an infra-red camera). The resulting images may be displayed on a display monitor 140 which is electrically coupled to a data acquisition and control computer system 138, the variations in color showing the area of blunt impact.

This thermal imaging method comprises placing the high-power RF coil 134 in proximity to the appliqué 96 and then activating the coil to generate an electromagnetic field. Excitation frequencies for the high-power RF coil 134 may be in the range of 100 to 400 kHz. This range has been found to create an electromagnetic field that penetrates composite material. It is well known that eddy currents are induced in a conductive medium by a changing magnetic field. For example, a changing magnetic field can result from relative motion of the coil and the conductive medium; or due to variations of the electromagnetic field with time. The stronger the applied magnetic field, or the greater the electrical conductivity of the conductive medium, or the greater the relative velocity of motion, the greater the eddy currents developed. In the application depicted in FIG. 6, the eddy currents induced by the varying magnetic field will be different depending on whether or not any area of the appliqué 96 has been impacted by a blunt object with sufficient pressure to rupture hollow microspheres in the impact area. As a result, the eddy currents in the impact area will be stronger than the eddy currents outside the impact area. The differences in the strengths of the eddy currents inside and outside the impact area will produce corresponding different degrees of heating. The coil's excitation current can be pulse width modulated to allow for controlled heating.

The method further comprises thermal imaging of the heated area. More specifically, a thermal image of the conductive medium is created to reveal electromagnetic state information about the electrically conductive media in the appliqué 96. In the embodiment depicted in FIG. 6, the thermal image is generated using a thermal imaging camera 136. In other embodiments, the thermal image may be created by placing a thermographic film on the surface of the composite component. The thermographic film is temperature-sensitive and generates an optically viewable representation of the heated area. Such a thermographic film is described in detail in U.S. Pat. No. 7,287,902.

As shown in FIG. 6, the high-power RF coil 134 is powered by a controllable power supply 142. Placing the powered RF coil 134 in proximity to the composite skin surface of fuselage 132 induces current flow in the appliqué 96 and associated local heating of the appliqué 96. The thermal imaging camera 136 is directed at the skin surface with a field of view encompassing all or part of the appliqué 96, to allow recording of the thermal gradient of the heated appliqué 96 after the RF coil 134 has been removed. A data acquisition and control computer system 138 records the data from the thermal imaging camera 136 and provides control of the controllable power supply 142 for various thermal imaging techniques, as will be described in greater detail subsequently.

For certain embodiments with differential imaging processes, initial (e.g., pre-blunt impact event) and final (e.g., post-blunt impact event) images of the appliqué 96 are captured. In each instance, power is applied to the induction coil 134 and, in a hand-operated embodiment, the inspector/operator waves the coil 134 over the area to be inspected. The desired motion of the coil 134 and its distance from the skin surface are dependent on the power level, RF frequency, shape and size of the coil 134. The coil's electro-magnetic field inductively generates eddy currents in any electrically conductive areas of the appliqué 96 and underlying skin. The eddy currents generated in the electrically conductive materials are of sufficient strength to generate heat depending upon local electrical paths. The thermal imaging camera 136 is used to image relative heating before and after a blunt impact event. The relative heating is determined for certain embodiments using differential thermal imaging by subtracting the initial image values from the final image values.

In the system depicted in FIG. 6, the thermal imaging camera 136 may comprise a focal plane array infra-red camera. The induced currents produced by the coil 134 constitute the excitation technique, generating thermal gradients that reveal any differences in the electromagnetic behavior of respective examined areas. The induced current heating can be generated in a pulsed manner in order to allow for controlled heating without damaging the structure underlying the appliqué 96. In addition, the frame captured by the thermal imaging camera 136 can be synchronized (by a synchronization unit 144 electrically coupled to the data acquisition and control computer system 138 and to the controllable power supply 142) with the current pulse supplied to the coil 134 so that an image can be obtained before the current is pulsed and then captured after the current has been pulsed. The data acquisition and control computer system 138 is programmed to control both the thermal imaging camera 136 and the power supply 142 as well as storage of data from the camera. Presentation of captured thermal imaging data is provided on the display monitor 140 and stored in memory for additional processing.

In alternative embodiments employing an automated system, the induction coil motion is accomplished using a three-axis positioning device with motion along the skin surface, coil excitation and thermal imaging controlled by the computer control system for synchronization of the data.

Figure 7A:
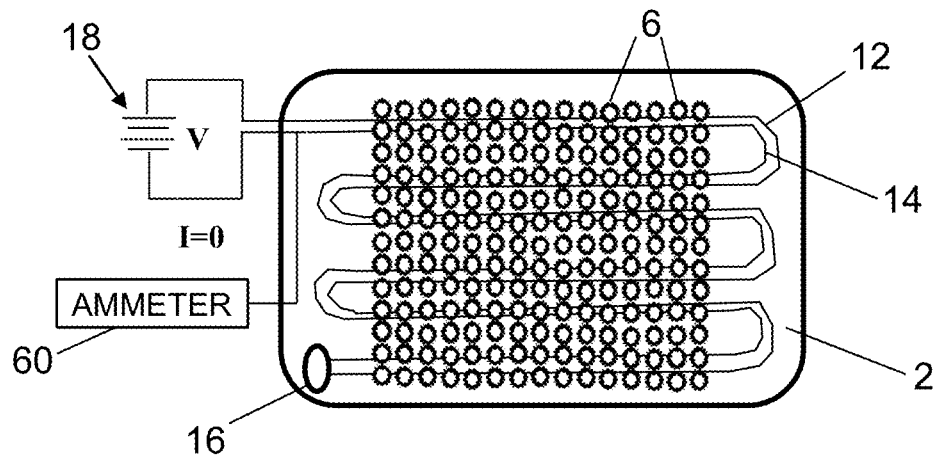
FIGS. 7A and 7B are diagrams representing top views of a blunt impact indicator system in accordance with another embodiment, comprising a substrate coated with rupturable microspheres filled with electrically conductive fluid, electrical conductors which are not electrically coupled when the microspheres are intact, and a voltage supply.
Figure 7B:
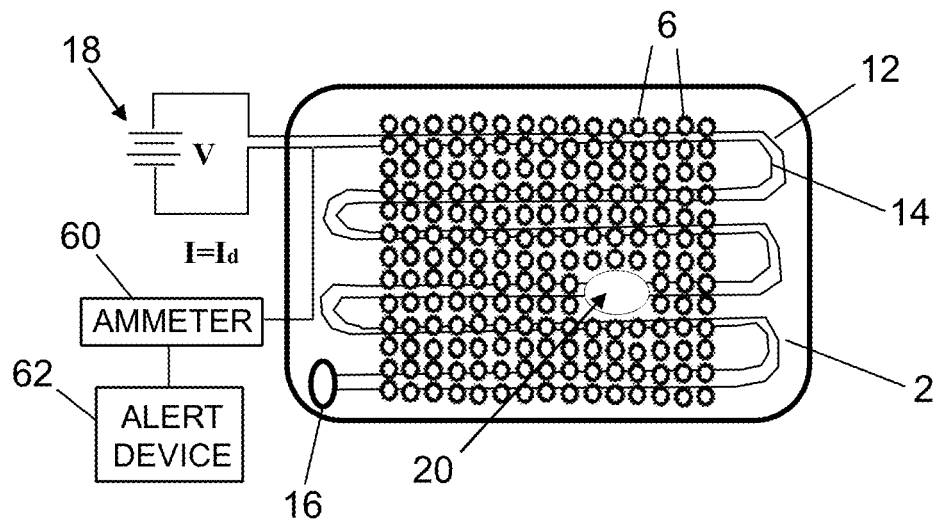

FIGS. 7A and 7B are diagrams representing top views of a blunt impact indicator system in accordance with another embodiment, comprising a substrate 2 coated with rupturable microspheres 6 filled with electrically conductive fluid, a pair of serpentine electrical conductors 12 and 14 which are not electrically coupled to each other (indicated by open circuit 16) when microspheres 6 are intact, and a voltage supply 18 (e.g., a battery). The electrical conductors 12 and 14 may comprise wires or other current paths embedded in or printed on the substrate 2. FIG. 7A shows the system when all microspheres 6 are intact and the current through electrical conductors 12, 14 is I=0, while FIG. 7B shows the system after some microspheres have been ruptured and electrically conductive fluid has been released to form a puddle or collection 20 of electrically conductive fluid. If the extent of the electrically conductive puddle or collection 20 is sufficient to electrically couple the electrical conductors 12 and 14 to each other, a circuit across the power and ground terminals of the voltage supply 18 will be closed. The electrical current I=$I_d$ flowing through the completed circuit can be detected by an ammeter 60 (or other current detector), which sends an alert signal to an alert device 62 to indicate an impact above a threshold defined by the microsphere shell strength.

In accordance with Ohm's Law, when the potential difference across the terminals of the voltage supply 18 (i.e., the terminal voltage) is constant, the electrical current $I_d$ will be inversely proportional to the resistance of the completed circuit. That resistance, in turn, is directly proportional to the length of the completed circuit, which means that the electrical current $I_d$ will be inversely proportional to the length of the completed circuit. If the positions of the wires are mapped, then the location of the impact can be determined from the current level measured by the ammeter 60.

Figure 8:
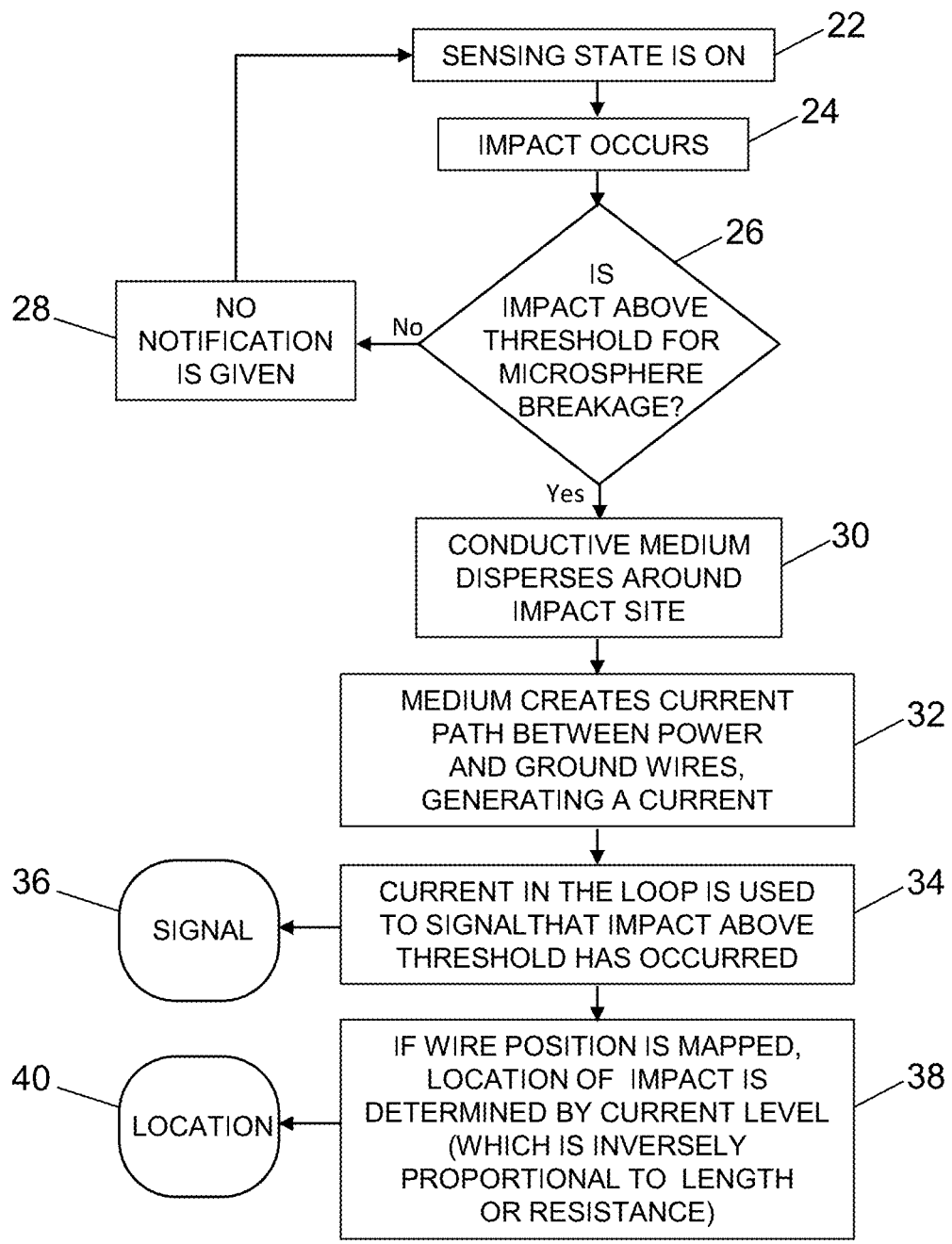
FIG. 8 is a flowchart showing steps of a method for providing a measure of the level (i.e., magnitude) and location of a blunt impact without direct visual indication using the system shown in FIGS. 7A and 7B.

FIG. 8 shows a process for providing a measure of the level (i.e., magnitude) and location of a blunt impact without direct visual indication using the system shown in FIGS. 7A and 7B. When a pair of electrical conductors are connected to the terminals of a voltage supply and not to each other, the sensing state is on (state 22). For the sake of illustration, it will be presumed that an impact has occurred (event 24). The response of the system will depend on whether the impact is above the threshold for microsphere breakage or not, as indicated in decision block 26 in FIG. 8. If the microspheres have not ruptured, then no notification is given (option 28) and the sensing state remains on (state 22). Conversely, if the microspheres have ruptured, then the electrically conductive fluid inside the hollow microspheres will disperse around the impact site (event 30). If a sufficient volume of electrically conductive fluid has been dispersed, then the electrically conductive fluid will create a current path between the power and ground wires which form the voltage terminals (event 32). The resulting electrical current in the completed circuit (i.e., loop) is detected by the current detector (step 34), which outputs a signal 36 indicating that an impact in excess of the threshold has occurred. Furthermore, if the positions of the electrical conductors (e.g., wires) has been mapped and if the current detector is in the form of an ammeter capable of measuring the current level in the completed circuit, then that ammeter will output a signal indicating the current level to an impact location processor. The impact location processor can input the current level into a look-up table that determines the location 40 of the impact relative to the mapped wires (step 38).

A DC voltage supply 18 (e.g., a battery that is off-board of the structure) is indicated in FIGS. 7A and 7B, with an in-line means to sense the current. The impact completes the circuit between the twin serpentine electrical conductors 12 and 14. Otherwise there is no circuit and no current measured. Since alternating current has less voltage drop over a line than direct current, a more efficient method would be to plug into an AC generator of some type that is off the structure.

Figure 9:
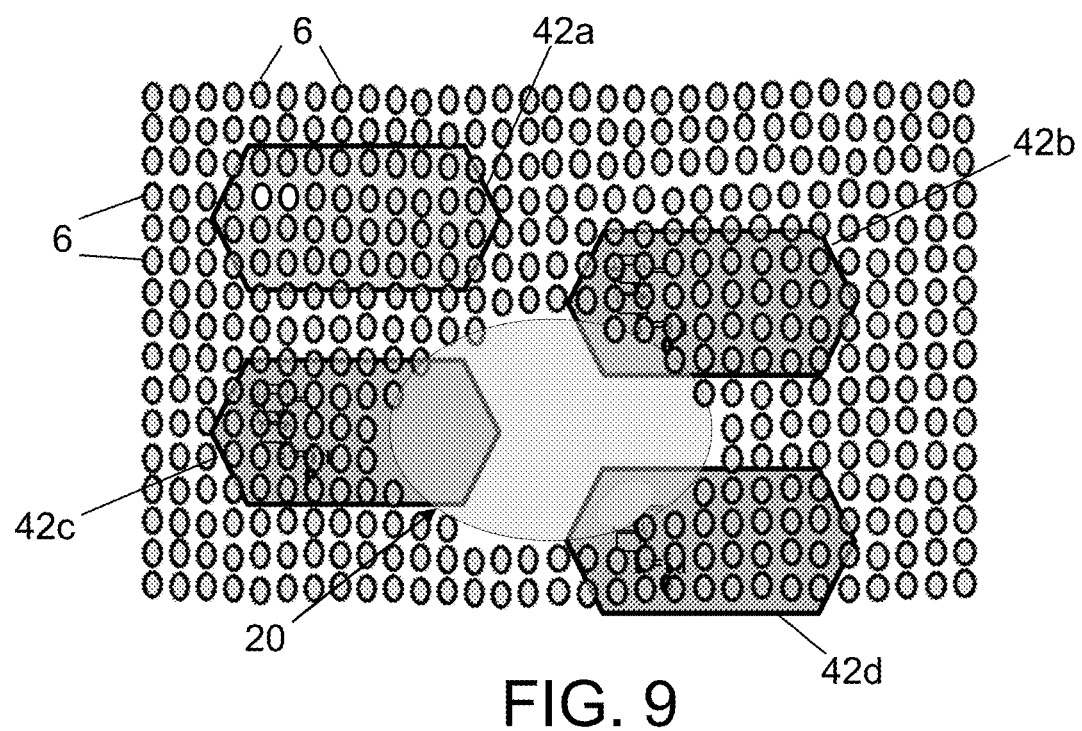
FIG. 9 is a diagram representing a top view of a blunt impact indicator comprising a multiplicity of passive RFID chips in accordance with an alternative embodiment.

FIG. 9 is a diagram representing a top view of a blunt impact indicator in accordance with an alternative embodiment. This blunt impact indicator works on the same principle (i.e., breaking microspheres to release electrically conductive fluid at an impact site to complete an electrical circuit) as the previous embodiment depicted in FIGS. 7A and 7B, but on a smaller scale. The embodiment depicted in FIG. 9 comprises a multiplicity of passive RFID chips 42a-42d adhered to and distributed over a surface of a substrate (i.e., a tape or an appliqué). A multiplicity of hollow microspheres 6 are adhered to or embedded in a surface of the substrate, with respective pluralities of microspheres 6 overlying respective RFID chips 42a-42d. In response to a blunt impact that produces pressure sufficient to rupture impacted microspheres, the microspheres at the impact site will rupture, releasing electrically conductive fluid 20 in an area that may overlap one or more RFID chips 42a-42d.

Figure 10:
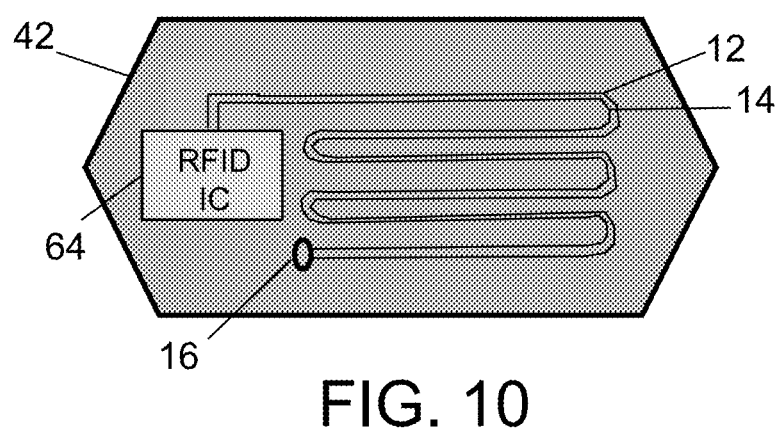
FIG. 10 is a diagram representing a top view (with a magnified scale) of a passive RFID chip of the type incorporated in the blunt impact indicator depicted in FIG. 9.

As depicted in FIG. 10, each passive RFID chip 42 preferably comprises an RFID integrated circuit 64 connected to a pair of serpentine electrical conductors 12 and 14 which, in the absence of electrically conductive fluid therebetween, are not electrically connected to each other. In response to the release of electrically conductive fluid, the electrical conductors 12 and 14 form a completed circuit, enabling these electrical conductors to serve as both antenna coils for communication with an RFID reader and sensing coils for detecting local areas in which impacts above a specified threshold have occurred. The threshold is preferably a function of the burst strength of the shells of the microspheres 8.

The RFID integrated circuit 64 performs the following functions: storing and processing information, modulating and demodulating a radio-frequency (RF) signal, collecting DC power from the incident reader signal, and other specialized functions. The electrical conductors 12 and 14, when electrically connected by electrically conductive fluid, serve as an antenna for receiving and transmitting RF signals. Unique RFID tag information is stored in a nonvolatile memory for each RFID chip. The RFID integrated circuit 64 includes either chip-wired logic or a programmed or programmable data processor for processing data.

Although FIG. 10 shows an embodiment in which the electrical conductors 12 and 14 are incorporated within the RFID chip 42, it is also possible to have the electrical conductors 12 and 14 printed on the tape or appliqué to which the RFID chips are attached. Blunt impact indicators in accordance with this alternative embodiment can provide more coverage using fewer RFID chips.

Upon the release of electrically conductive fluid from the hollow microspheres 8, the electrical conductors 12 and 14 will form a completed circuit in the manner previously described with reference to FIG. 7B. Again the magnitude of the current flowing in the completed circuit will be inversely proportional to the length of completed circuit. The response of the RFID integrated circuit 64 is changed by the released conductive fluid. When queried, the passive RFID chip 42 will have a different frequency response due to a different impedance in the electrical conductors 12 and 14. The electrical conductors 12 and 14, when electrically connected, serve as the antenna for communication with another device, such as an RFID reader. A change in impedance, due to the impact scenario discussed, will cause a shift in the antenna response that can be sensed.

In accordance with the embodiment depicted in FIG. 9, each RFID chip 42a-42d is of the passive variety. When a passive RFID chip passes through the field of a scanning antenna, the electrical conductors 12 and 14 (see FIG. 10) of an RFID chip 42 pick up RF signals output by the scanning antennae and then return the signal with some additional data, such as a unique serial number or other customized information. More specifically, the serpentine electrical conductors 12 and 14 generate an electromagnetic field from which the RFID chip draws power, thereby energizing its circuits. The transceiver of the RFID circuit 64 then sends identifying information encoded in and read from the nonvolatile memory.

Figure 11:
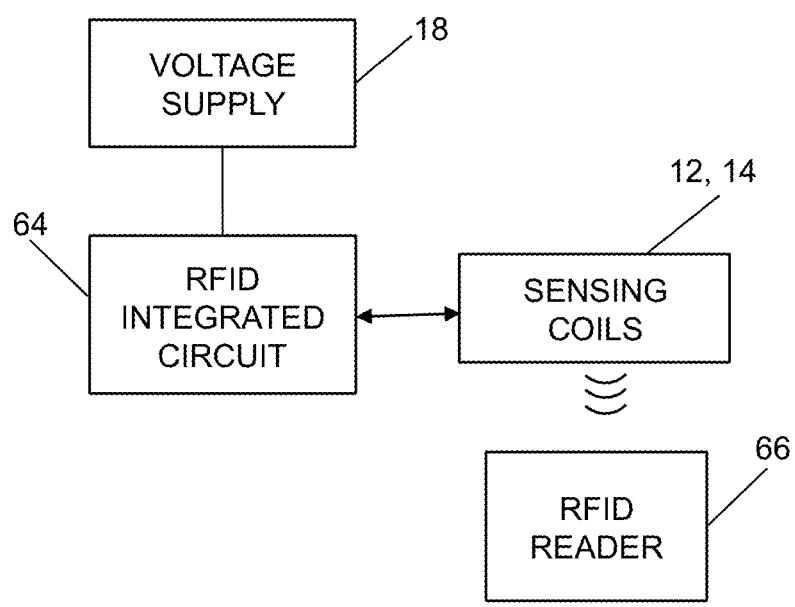
FIG. 11 is a block diagram showing components of a system comprising an RFID reader capable of reading blunt impact data stored in active RFID chips installed on a structure.

Alternatively, the RFID chips may be of the active type, meaning that each chip is powered by its own voltage supply (e.g., a battery). FIG. 11 shows components of a system comprising an RFID integrated circuit 64 powered by a voltage supply 18 and an RFID reader 66 capable of receiving sensor data transmitted by the RFID integrated circuit 64. As previously described, when queried by the RFID reader 66, an RFID chip adhered to the monitored structure within an impact area will have a different frequency response due to a change in impedance in the electrical conductors 12 and 14. The electrical conductors 12 and 14, when electrically connected, serve as both impact sensing coils and an antenna for communication with the RFID reader 66. The RFID reader 66 emits radio waves depending upon its power output and the radio frequency used. When an RF chip with released electrically conductive fluid passes through the electromagnetic zone of the RFID reader 66, the RFID integrated circuit 64 detects the reader's activation signal. The RFID reader 66 decodes the chip identification data encoded in the non-volatile memory of the RFID integrated circuit 64 and that chip identification data is passed (along with data representing the changed frequency response of the RFID chip) to a host computer for processing. In the case where a plurality of RFID chips are mapped on a tape or appliqué adhered to a structure, the identities of any RFID chips having frequency responses indicative of a blunt impact can be processed to determine their locations and the extent of the impact area.

Figure 12:
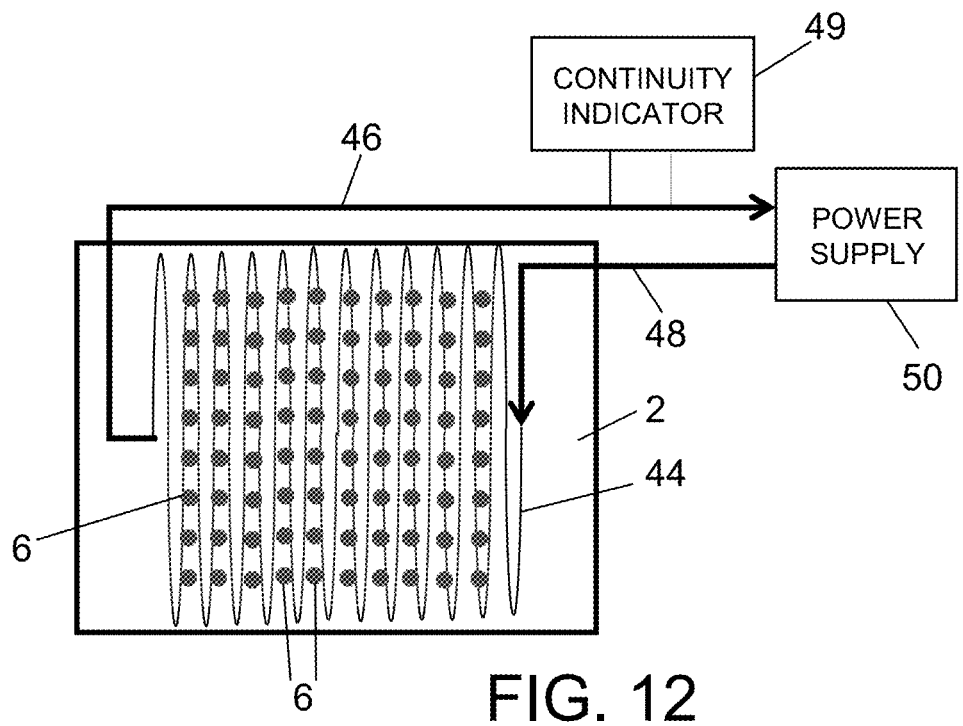
FIG. 12 is a diagram representing a top view of a blunt impact indicator comprising a matrix of breakable electrical conductors (e.g., wires) in accordance with another embodiment.

A blunt impact indicator in accordance with an alternative embodiment is schematically depicted in FIG. 12. Optionally, this indicator system may incorporate a layer or coating having a multiplicity of hollow microspheres 6 (filled with colored fluid) embedded therein, for a purpose to be described later. In the implementation illustrated in FIG. 12, a serpentine electrical conductor 44 made of breakable material (e.g., wire) is disposed in or on a substrate 2 (e.g., a tape or an appliqué), which substrate in turn is applied on a surface of a structure to be monitored. In the alternative, a grid of electrical conductors having some other geometry (e.g., a spiral) can be employed.

As shown in FIG. 12, the serpentine electrical conductor 44 has a pair of terminals respectively connected to the voltage terminals of a power supply 50. Therefore, when the serpentine electrical conductor 44 is completely intact, an electrical current flows through a continuity indicator 49 by way of electrical conductors 48, 44 and 46 (which are connected in series). In one implementation, the continuity indicator 49 could be as simple as a light bulb or LED or more complex, as in a computerized program that is activated when the voltage drops from the loss of continuity.

Figure 13:
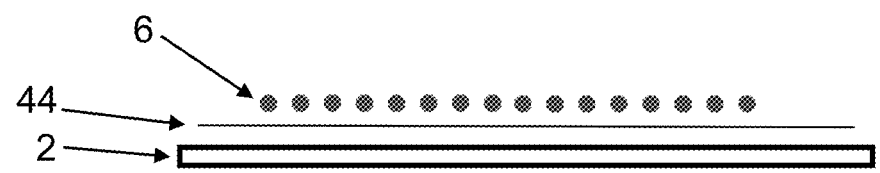
FIG. 13 is a diagram representing a sectional view of the blunt impact indicator depicted in FIG. 12.

In response to a blunt impact in an area overlying the serpentine electrical conductor 44, one or more turns of electrical conductor 44 may be broken, in which case electrical current will cease to flow through the continuity indicator 49. In this state, the continuity indicator 49 indicates to the technician that a blunt impact event has occurred, but does not indicate the location or extent of the impact site. Optionally, if microspheres 6 (filled with colored fluid) have been distributed over the area occupied by the serpentine electrical conductor 44 prior to an impact (as depicted in the sectional view presented in FIG. 13), any impact that exerts sufficient pressure will also cause one or more microspheres 6 to rupture, in which case released colored fluid provides to the technician a visual indication of the location and extent of the impact site.

In accordance with an alternative implementation, the breakable electrical conductors may take the form of an electrically conductive mesh on a substrate adhered to a structure. In the event of a blunt impact of sufficient force to break some of the breakable electrical conductors, the area of breakage can be detected using an induction coil alone or in conjunction with a thermal imaging camera, as previously described.

Figure 14:
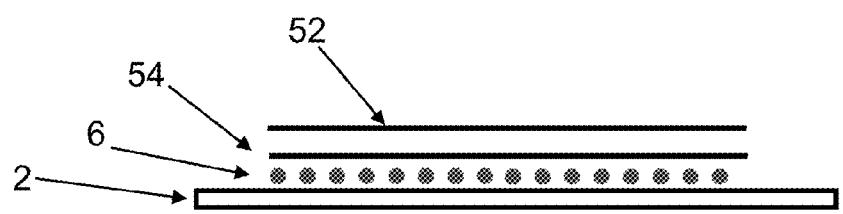
FIG. 14 is a diagram representing a sectional view of a blunt impact indicator comprising pH-sensitive paper and hollow microspheres filled with fluid having a pH level that will produce a color change that is visible under normal lighting or other lighting (UV, IR, etc.) when the fluid is released from ruptured microspheres.

FIG. 14 is a diagram representing a sectional view of a blunt impact indicator using fluid-filled microspheres in accordance with another embodiment. In this case the indicator comprises: a substrate 2 (i.e., a tape or appliqué) which will be adhered to a surface of a structure to be monitored; a multiplicity of hollow microspheres 6 distributed in a coating or layer of material (not shown) which is laminated to the substrate 2; a sheet of pH-sensitive paper 54 which is laminated to the coating or layer containing embedded microspheres 6; and a transparent protective layer 52 which covers and protects the pH-sensitive paper 54. In one implementation, the hollow microspheres 6 are filled with fluid having a pH level that will produce a color change on the pH-sensitive paper 54 that is visible under normal lighting or other lighting (UV, IR, etc.) when fluid is released from ruptured microspheres. If all of the shells of microspheres 6 have the same burst strength, then the portion of the pH-sensitive paper 54 which changes color will indicate the location and extent of an area in which the pressure exerted upon impact exceed a threshold corresponding to the burst strength.

In accordance with an alternative implementation, the shells of the hollow microspheres 6 may have different burst strengths and be filled with fluids having different pH levels. For example, a first multiplicity of microspheres having a relatively low burst strength can be filled with fluid having a first pH level, and a second multiplicity of microspheres having a relatively high burst strength can be filled with fluid having a second pH level different than the first pH level. If the indicator is subjected to an impact sufficient to rupture the first multiplicity of microspheres but not rupture the second multiplicity of microspheres, then only fluid having the first pH level will be released, thereby causing the pH-sensitive paper 54 to change coloration from its original color to a first color. If the indicator is subjected to an impact sufficient to rupture the first and second multiplicities of microspheres, then fluid having the first pH level and fluid having the second pH level will be released, thereby causing the pH-sensitive paper 54 to change coloration from its original color to a second color different than the first color.

In some embodiments, variations in rupture resistance (i.e., burst strength) of the microsphere shells may be achieved by varying the thickness of the walls in the respective multiplicities of microspheres. In the example given above, the wall thickness of the microspheres of the first multiplicity may be less than the wall thickness of the microspheres of the second multiplicity. In other embodiments, variations in the rupture resistance of the microsphere shells may be achieved using alternative methods or techniques known by those skilled in the art. Thus, the leaked fluid may both mark the location and indicate the magnitude of the blunt impact force which was applied to the surface.

For the case when one specifically does not want the blunt impact indication to be readily visible, the microspheres may be filled with clear UV or IR fluorescing dyes which, when released, are not visible to the naked eye, but can be found using UV or IR light. In accordance with another embodiment, a clear fluid is contained inside the microspheres, which clear fluid, when released, only becomes visible when chemically activated by a developer spray applied by the inspector. In accordance with an alternative embodiment, the microspheres contain at least two separate liquids that react when they come in contact with each other, creating a colored indicator.

Figure 15:
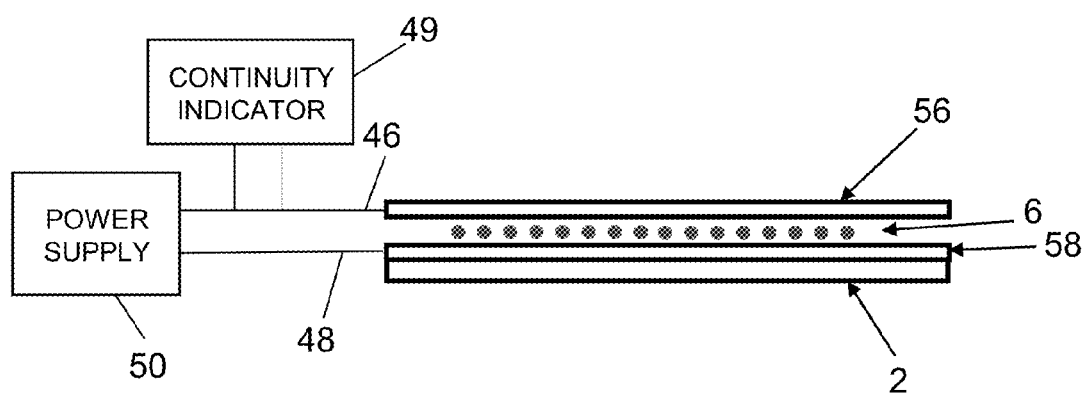
FIG. 15 is a diagram representing a sectional view of a portion of a blunt impact indicator tape in accordance with a further embodiment.

FIG. 15 is a diagram representing a sectional view of a portion of a blunt impact indicator tape in accordance with yet another embodiment. A multiplicity of hollow microspheres 6, filled with electrically conductive fluid, are embedded in a layer of dielectric material (not shown), which dielectric layer is sandwiched between a pair of mutually confronting electrically conductive layers 56 and 58, which form a large capacitor. The electrically conductive layers 56 and 58 are respectively electrically coupled to the voltage terminals of a power supply 50 and to respective terminals of a continuity indicator 49 by way of electrical connectors 46 and 48. When the microspheres 6 remain intact, there will be no electrical current flowing from one of the electrically conductive layers 56 or 58 to the other layer due to the absence of electrically conductive fluid in the space separating the electrically conductive layers 56 and 58. Conversely, if the number of microspheres ruptured during a blunt impact is sufficient to release enough electrically conductive fluid to bridge the electrically conductive layers 56 and 58, then electrical current can flow from one of electrically conductive layers 56 or 58 to the other. This flow of electrical current, indicative of a blunt impact, will turn on the continuity indicator 49. As previously noted, the continuity indicator 49 may be a light bulb or LED or may be a computerized program that is activated when electrical current flows through the completed circuit.

In accordance with alternative embodiments that avoid indications which are readily visible by a casual observer, the microspheres may be filled with clear UV or IR fluorescing dyes, which are released, and are not visible to the naked eye, but can be found using UV or IR light; or they may be filled with a clear fluid, which when released, only becomes visible when chemically activated by a developer spray applied by the inspector.

In accordance with a further alternative embodiment, the microspheres may be filled with at least two liquids which are separate prior to microsphere rupture and then react with each other when brought into contact with each other, thereby creating a colored (i.e., visible) indicator.

Figure 16:
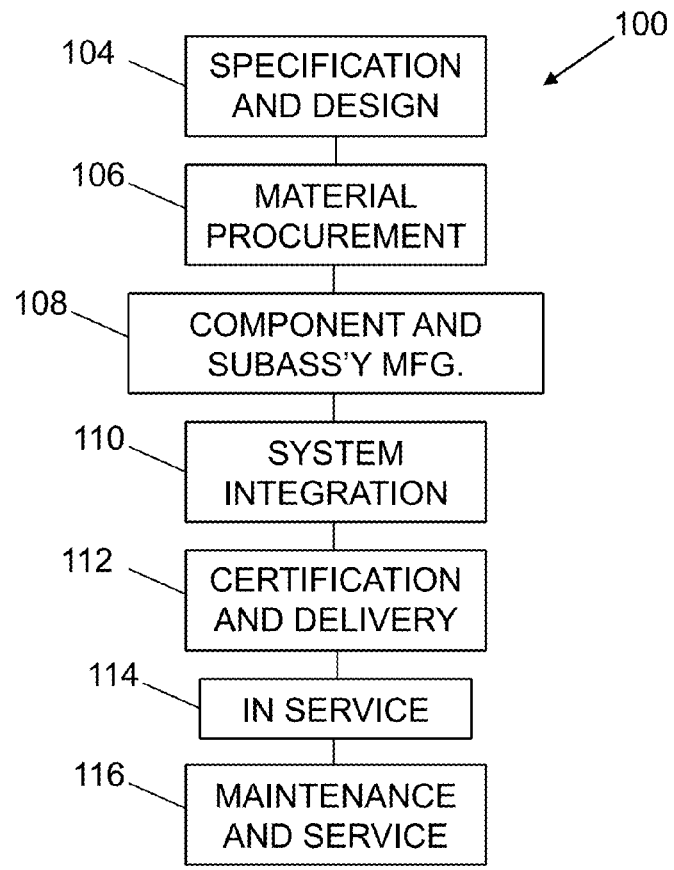
FIG. 16 is a flow diagram of an aircraft production and service methodology.
Figure 17:
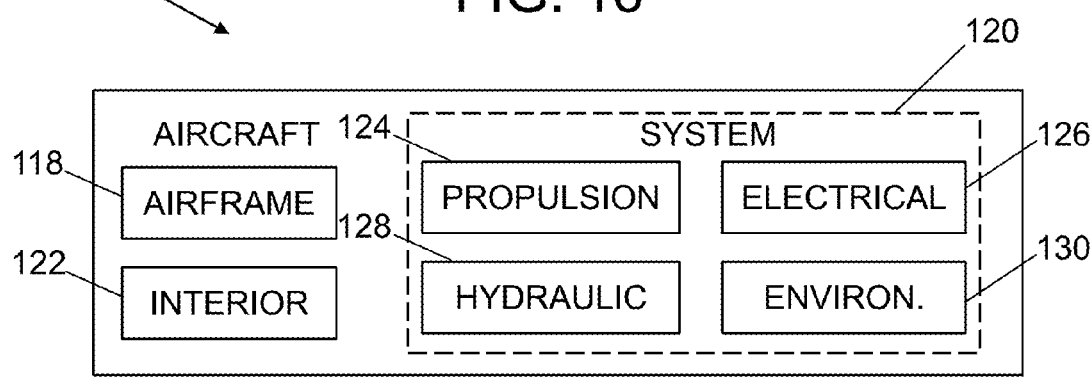
FIG. 17 is a block diagram showing systems of an aircraft.

Each of the systems and methods disclosed above may be employed in an aircraft manufacturing and service method 100 as shown in FIG. 16 for monitoring or indicating high-energy blunt impacts on an aircraft 102 as shown in FIG. 17. During pre-production, exemplary method 100 may include specification and design 104 of the aircraft 102 and material procurement 106. During production, component and subassembly manufacturing 108 and system integration 110 of the aircraft 102 takes place. Thereafter, the aircraft 102 may go through certification and delivery 112 in order to be placed in service 114. While in service by a customer, the aircraft 102 is scheduled for routine maintenance and service 116 (which may also include modification, reconfiguration, refurbishment, and so on).

Each of the processes of method 100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 17, the aircraft 102 produced by exemplary method 100 may include an airframe 118 with a plurality of systems 120 and an interior 122. Examples of high-level systems 120 include one or more of the following: a propulsion system 124, an electrical system 126, a hydraulic system 128, and an environmental control system 130. Any number of other systems may be included.

The systems and methods embodied herein may be employed during one or more of the stages of the production and service method 100. Also, one or more system embodiments, method embodiments, or a combination thereof may be utilized during the production stages 108 and 110, for example, by providing a measure of the magnitude and location of a high-energy blunt impact on a workpiece during the process of assembling an aircraft 102. Similarly, one or more of system embodiments, method embodiments, or a combination thereof may be utilized while the aircraft 102 is in service, for example and without limitation, during maintenance and service 116.

While systems and methods for have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The method claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

As used in the claims, the phrase "disposed in proximity to a surface of a substrate" in connection with microspheres should be construed to encompass at least the following species: (1) attaching microspheres to the surface; and (2) embedding microspheres in a coating which is applied on the surface.

The invention claimed is:

1. A blunt impact indicator device comprising:
a substrate comprising first and second surfaces;
a multiplicity of rupturable shells disposed in proximity to said first surface of said substrate, the shells having an electrically conductive fluid disposed in an internal volume of the shells;
an antenna comprising first and second electrical conductors which are not electrically coupled to each other in the absence of electrically conductive fluid; and
a radio-frequency identification circuit comprising a transceiver connected to said first and second electrical conductors,
wherein said first and second electrical conductors are disposed on one side of said first surface of said substrate and configured and spaced so that said first and second electrical conductors can be electrically coupled to each other in the presence of electrically conductive fluid released from said multiplicity of shells, and
wherein any response transmitted by the transceiver will have a frequency which is a function of an impedance of the antenna when the first and second serpentine electrical conductors are electrically coupled to each other by electrically conductive fluid escaped from the multiplicity of shells.

2. The blunt impact indicator device as recited in claim 1, wherein said shells are hollow microspheres made of dielectric material.

3. The blunt impact indicator device as recited in claim 1, further comprising a layer of adhesive on said second surface of said substrate.

4. The blunt impact indicator device as recited in claim 1, wherein said substrate is in the form of a tape or an appliqué.

5. The blunt impact indicator device as recited in claim 1, wherein said first and second electrical conductors are serpentine.

6. The blunt impact indicator device as recited in claim 1, wherein said radio-frequency identification circuit further comprises non-volatile memory storing information which uniquely identifies said radio-frequency identification circuit.

7. A The blunt impact indicator device comprising:
a substrate;
a breakable electrical conductor disposed on or embedded in said substrate and having first and second terminals;
a voltage supply connected to said first and second terminals of said breakable electrical conductor;
a continuity indicator electrically connected to said breakable electrical conductor;
a multiplicity of rupturable shells disposed in proximity to a surface of said substrate, said shells being distributed over an area encompassing said breakable electrical conductor, each shell having an internal volume; and
an electrically conductive fluid disposed in the internal volumes of respective shells of said multiplicity of shells.

8. The blunt impact indicator device as recited in claim 7, wherein said breakable electrical conductor has a serpentine or spiral configuration.

9. A method for monitoring a structure for damage due to blunt impact, comprising:
    attaching a substrate to a surface of the structure, the substrate comprising a multiplicity of rupturable shells adhered thereto or embedded therein, each shell having an internal volume, and an electrically conductive fluid disposed in the internal volumes of respective shells of said multiplicity of shells; and
    detecting a change in electrical conductivity of the substrate,
    wherein said detecting a change in electrical conductivity of the substrate comprises:
    placing a coil in proximity to the substrate;
    causing alternating current to flow through the coil during first and second time intervals, a magnitude of said alternating current and a distance separating the coil from the substrate being selected for inducing eddy currents in the substrate; and
    measuring any difference between a first impedance of the coil during said first time interval and a second impedance of the coil during said second time interval.

10. The method as recited in claim 9, wherein said detecting a change in electrical conductivity of the substrate further comprises:
    determining whether a difference between said first and second impedances is greater than a specified threshold; and
    performing non-destructive inspection in the area of the structure which the coil is in proximity to if said difference between said first and second impedances is greater than said specified threshold.

11. A method for monitoring a structure for damage due to blunt impact, comprising:
    attaching a substrate to a surface of a structure, the substrate comprising a multiplicity of rupturable shells disposed in proximity to a surface of the substrate, each shell having an internal volume, and an electrically conductive fluid disposed in the internal volumes of respective shells of said multiplicity of shells; and
    detecting a change in thermal state of the substrate.

12. The method as recited in claim 11, wherein said detecting a change in thermal state of the substrate comprises performing the following steps during first and second intervals of time which do not overlap:
    (a) placing a coil in proximity to the substrate;
    (b) causing alternating current to flow through the coil while the coil is in proximity to the substrate;
    (c) after the substrate has been heated in an area during step (b) due to eddy currents induced in the electrically conductive fluid by the alternating current in the coil, removing the coil; and
    (d) after the coil has been removed, acquiring a thermal image of the area of the heated substrate using a thermal imaging camera.

13. The method as recited in claim 12, wherein said detecting a change in thermal state of the substrate further comprises:
    comparing a first thermal image acquired during said first interval of time with a second thermal image acquired during said second interval of time.

14. The method as recited in claim 13, further comprising displaying an image representing differences between said first and second thermal images.

15. A method for monitoring a structure for damage due to blunt impact, comprising:
    placing a radio-frequency identification circuit and first and second serpentine electrical conductors on a substrate, the first and second serpentine electrical conductors having respective first terminals electrically connected to respective terminals of the radio-frequency identification circuit and respective second terminals which are not electrically connected to each other;
    placing a multiplicity of rupturable shells over the first and second serpentine electrical conductors, each shell having an internal volume at least partially filled with electrically conductive fluid; and
    interrogating the radio-frequency identification circuit by transmitting a radio-frequency signal through a volume of space intersected by radio-frequency identification circuit,
    wherein any response to the interrogation by the radio-frequency identification circuit will have a frequency which is a function of an impedance of an antenna formed if the first and second serpentine electrical conductors are electrically coupled to each other by electrically conductive fluid escaped from the multiplicity of shells.

16. A system for monitoring a structure for damage due to blunt impacts, comprising:
    a substrate comprising first and second surfaces;
    a multiplicity of radio-frequency identification circuits adhered to said first surface of said substrate;
    a multiplicity of rupturable shells comprising respective sets of rupturable shells overlying respective radio-frequency identification circuits, each shell having electrically conductive fluid disposed in an internal volume thereof; and
    a multiplicity of antennas respectively connected to said multiplicity of radio-frequency identification circuits,
    wherein each of said antennas comprises first and second electrical conductors which are configured and spaced so that said first and second electrical conductors can be electrically coupled to each other in the presence of electrically conductive fluid released from said multiplicity of shells;
    wherein each radio-frequency identification circuit comprises a respective transceiver connected to said first and second electrical conductors of a respective antenna; and
    wherein any response transmitted by a transceiver will have a frequency which is a function of an impedance of the respective antenna when said first and second electrical conductors are electrically coupled to each other by electrically conductive fluid escaped from the multiplicity of shells.

17. The system as recited in claim 16, further comprising:
    a radio-frequency reader capable of acquiring data representing changes in frequency response of said radio-frequency identification circuit; and
    a host computer configured for processing acquired data received from said radio-frequency reader to determine a location and an extent of a blunt impact based on identities of any radio-frequency identification circuits having a changed frequency response.

* * * * *